(12) United States Patent
Hayashi

(10) Patent No.: US 9,518,997 B2
(45) Date of Patent: Dec. 13, 2016

(54) BLOOD COAGULATION SYSTEM ANALYZER, AND BLOOD COAGULATION SYSTEM ANALYSIS METHOD AND PROGRAM

(75) Inventor: Yoshihito Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 13/142,991

(22) PCT Filed: Jan. 7, 2010

(86) PCT No.: PCT/JP2010/050367
§ 371 (c)(1),
(2), (4) Date: Jun. 30, 2011

(87) PCT Pub. No.: WO2010/079845
PCT Pub. Date: Jul. 15, 2010

(65) Prior Publication Data
US 2012/0035450 A1 Feb. 9, 2012

(30) Foreign Application Priority Data

Jan. 8, 2009 (JP) .................................. 2009-002650
Dec. 24, 2009 (JP) .................................. 2009-293156

(51) Int. Cl.
*A61B 5/00* (2006.01)
*G01N 33/49* (2006.01)
(Continued)

(52) U.S. Cl.
CPC .......... *G01N 33/86* (2013.01); *G01N 33/4905* (2013.01); *G01N 27/026* (2013.01)

(58) Field of Classification Search
USPC .................................. 436/69; 600/368, 369
See application file for complete search history.

(56) References Cited

U.S. PATENT DOCUMENTS

2004/0072357 A1* 4/2004 Stiene et al. ..................... 436/69
2007/0073115 A1* 3/2007 Hwang .............. A61B 5/14532
600/309
(Continued)

FOREIGN PATENT DOCUMENTS

JP 56-744 B1 1/1981
JP 2004 522146 7/2004
(Continued)

OTHER PUBLICATIONS

Connelly, J. A., & Buckler, M. J. (1975). The continuous measurement of resistivity and permittivity of human blood plasma during coagulation. Medical and biological engineering, 13(4), 523-530.*

(Continued)

*Primary Examiner* — Michael Kahelin
*Assistant Examiner* — Mitchell E Alter
(74) *Attorney, Agent, or Firm* — Oblon, McClelland, Maier & Neustadt, L.L.P.

(57) ABSTRACT

A blood coagulation system analysis device capable of analyzing a blood coagulation system with high accuracy, and a method and a program for analysis of a blood coagulation system are proposed.
The blood coagulation system is observed as a temporal change in permittivity before the viscoelasticity manifestation timing (timing at which blood starts to clot from the viewpoint of viscoelasticity (in greater detail, timing at which active polymerization of fibrin monomers starts)). A permittivity of blood which is positioned between a pair of electrodes is measured at predetermined time intervals after the anticoagulant effect acting on the blood is ended, and from the measurement result, a degree of the action of the blood coagulation system is analyzed.

10 Claims, 12 Drawing Sheets

(51) Int. Cl.
  *G01N 33/86* (2006.01)
  *G01N 27/02* (2006.01)

(56) References Cited

U.S. PATENT DOCUMENTS

2008/0063566 A1* 3/2008 Matsumoto et al. ........ 422/68.1
2008/0262740 A1* 10/2008 Potter .................... C12Q 1/006
                                                             702/19

FOREIGN PATENT DOCUMENTS

| JP | 2006 349684 | 12/2006 |
| JP | 4027596 B2 | 12/2007 |
| JP | 2008 215901 | 9/2008 |
| RU | 1 720 386 C | 3/1995 |

OTHER PUBLICATIONS

N. C. Hightower, "Resistivity and Permittivity Characteristics of Human Blood Plasma During Coagulation" Georgia Institute of Technology, Aug. 1970.*
Irimajiri et al. "Dielectric monitoring of rouleaux formation in human whole blood: a feasibility study." Biochimica et Biophysica Acta, vol. 1290. pp. 207-209 (1996).
Asami. "Sekkekkyu Rensen no Yuden Spectrum." 29$^{th}$ Abstracts of Annual Meeting of Membrane Society of Japan. p. 31 (2007).
International Search Report issued Apr. 13, 2010 in PCT/JP10/50367 filed Jan. 7, 2010.
Combined Chinese Office Action and Search Report issued Sep. 23, 2013 in Patent Application No. 201080003940.6 (with English language translation).
Japanese Office Action dated Feb. 2, 2014, in Japanese Patent Application No. 2009-293156 (with English translation).
Office Action issued Aug. 12,2014, in Japanese Patent Application No. 2009-293156 with English translation.
Combined Chinese Office Action and Search Report issued Dec. 3, 2014 in Patent Application No. 201080003940.6 (with English language translation).
Notification of Reason for Refusal issued Mar. 15, 2016 in Japanese Patent Application No. 2014-229739 (with English language translation).
A. G. Mungall, et al., "Measurement of the Dielectric Properties of Blood" IRE Transactions on Bio-Medical Electronics, 1961, pp. 109-111.
Helen Berney, et al., "Impedance Measurement Monitors Blood Coagulation" Analog Dialogue, vol. 42, No. 3, 2008, pp. 7-9.
N. Spence, "Electrical impedance measurement as an endpoint detection method for routine coagulation tests" British Journal of Biomedical Science, vol. 59, No. 4, 2002, pp. 223-227.
Akihiko Irikou, et al., "Red Blood Cell Agglutination (Formation of Nummular Masses) from Aspect of Dielectric Motion of All Blood" Bioengineering, vol. 78, No. 5, 2000, pp. 162-165.
Japanese Office Action issued Nov. 10, 2015 for Japanese Patent Application 2014-229739 (with English machine translation).
Irimajiri et al. "Zenketsu no Yudo Kyodo kara Mita Sekkekkyu Gyoshu (Rensen Keisei)" Journal of the Society for Bioscience and Bioengineering, vol. 78, No. 5. pp. 162-165 (2000).
Irimajiri et al. "Zenketsu no Admittance Keisoku ni Yoru Sekkekkyu Gyoshu (Rensen Keisei) Kei no Shisaku." Annual Report, Nakatani Foundation of Electronic Measuring Technology Advancement, vol. 13. pp. 62-66 (1999).

\* cited by examiner

BLOOD COAGULATION SYSTEM ANALYZER, AND BLOOD COAGULATION SYSTEM ANALYSIS METHOD AND PROGRAM

TECHNICAL FIELD

The present invention relates to a field relating to a technique of obtaining information relating to blood coagulation from the permittivity of blood.

BACKGROUND ART

In the past, prothrombin time and activated partial thromboplastin have been widely known as blood coagulation system tests. In addition, these tests are important for an examination of blood coagulation factor deficiency syndrome or the like and monitoring of blood to which an anticoagulant is applied, and methods of standardizing the tests have been proposed (for example, see PTL 1).

CITATION LIST

[PTL 1] JP-A-2006-349684

SUMMARY OF INVENTION

However, the tests are not for (quantitatively) observing the degree of ease of clotting of blood, but for observing in a fragmentary manner (qualitatively) whether or not coagulation is completed within a time considered as normal under the conditions where the coagulation reaction is accelerated by adding an excessive amount of a coagulation initiator. In other words, the tests are methods for evaluating a risk (bleeding tendency) caused by difficulty of clotting of blood, and in this method, a risk (thrombotic tendency) caused by ease of clotting of blood cannot be evaluated. Observing (quantitatively) a degree of ease of clotting of blood is important because it has advantages such as a large amount of information in comparison to observing in a fragmentary manner, and in recent years, analyzing a blood coagulation system with high accuracy has been in more demand than observing in a fragmentary manner.

The invention is contrived in view of the above-described points and is to propose a blood coagulation system analysis device, and a method and a program for analysis of a blood coagulation system, capable of analyzing a blood coagulation system with high accuracy.

In order to solve such problems, the invention relates to a blood coagulation system analysis device including: a pair of electrodes; application means for applying an alternating voltage to the pair of electrodes at predetermined time intervals; measurement means for measuring a permittivity of blood which is positioned between the pair of electrodes; and analysis means for analyzing a degree of the action of a blood coagulation system by using the permittivity of blood which is measured at the time intervals after the anticoagulant effect acting on the blood is ended.

In addition, the invention relates to a blood coagulation system analysis method including: an application step of applying an alternating voltage to a pair of electrodes at predetermined time intervals; a measurement step of measuring a permittivity of blood which is positioned between the pair of electrodes; and an analysis step of analyzing a degree of the action of a blood coagulation system by using the permittivity of blood which is measured at the time intervals after the anticoagulant effect acting on the blood is ended.

In addition, the invention relates to a program to cause: an application portion which applies an alternating voltage to apply an alternating voltage to a pair of electrodes at predetermined time intervals; a measurement portion which measures a permittivity to measure a permittivity of blood which is positioned between the pair of electrodes; and an analysis portion which analyzes a blood coagulation system to analyze a degree of the action of a blood coagulation system by using the permittivity of blood which is measured at the time intervals after the anticoagulant effect acting on the blood is ended.

The blood coagulation system appears as a temporal change in permittivity before a timing (timing at which active polymerization of fibrin monomers starts) at which blood starts to clot from the dynamic viewpoint of viscoelasticity.

Regarding this point, since the invention uses the permittivity which is measured after an anticoagulant effect acting on the blood is ended, the process before the timing at which the blood starts to clot from the dynamic viewpoint of viscoelasticity can be clearly observed.

Accordingly, the invention can analyze the action of the blood coagulation system at an early stage by a temporal change in permittivity before the timing at which blood starts to clot from the dynamic viewpoint of viscoelasticity, and as a result, the degree of accuracy of the analysis can be increased in comparison to the conventional case as much as the movement of the blood coagulation system at an early stage is determined by a temporal change in permittivity. In addition, it is possible to analyze the degree of the action of the blood coagulation system earlier than in the conventional case.

DESCRIPTION OF EMBODIMENTS

Hereinafter, embodiments of the invention will be described. The description thereof will be given in the following order.

<1. Electric Characteristics of Cell>
<2. Consideration of Dielectric Spectrum of Blood Coagulation System>
[2-1. Method of Experiment]
[2-2. Experimental Results]
<3. Embodiments>
[3-1. Configuration of Blood Coagulation System Analysis Device]
[3-2. Order of Blood Coagulation System Analysis Process]
[3-3. Effects and the like]
<4. Other Embodiments>

1. Electric Characteristics of Cell

Figure 1:
FIG. 1 schematically shows the relationships between ions of a cell and an electric field, that is, the relationship (A) absence of the electric field and the relationship (B) presence of the electric field.

Positive ions and negative ions are included in a cell (FIG. 1(A)). When the cell is in an alternating electric field, these ions move (follow) in accordance with a change in the positive and negative directions in the alternating electric field. In this case, since the cell membrane has high insulating properties, the positive ions and the negative ions are unevenly distributed in the interface between the cell membrane and the cell cytoplasm, and ionic interfacial polarization occurs (FIG. 1(B)).

Figure 2:
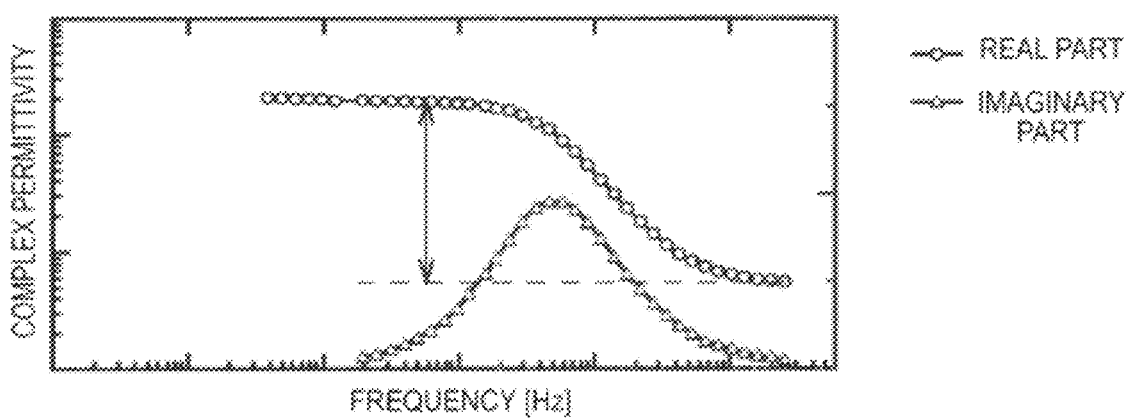
FIG. 2 is a graph showing a simulated complex permittivity spectrum.

Here, the simulated dielectric spectrum of a cell suspension which is quoted in references and the like is shown in FIG. 2. As can be seen from this FIG. 2, when the frequency of the alternating electric field is sufficiently low, interfacial polarization occurs in the interface between the cell membrane and the cell cytoplasm in the cell, and thus the real part of a complex permittivity is obtained as a large value. Hereinafter, the real part of the complex permittivity will be referred to as permittivity.

On the other hand, when the frequency of the alternating electric field is about several tens [MHz], switching between positive and negative in the alternating electric field occurs before the movement of the positive ions and the negative ions to the interface between the cell membrane and the cell cytoplasm. That is, the ionic interfacial polarization cannot follow a change in the alternating electric field.

Accordingly, the higher the frequency of the alternating electric field, the smaller the value of the permittivity. The phenomenon of a reduction in permittivity is referred to as "dielectric relaxation", and in a portion where the dielectric relaxation occurs, the imaginary part of the complex permittivity increases. The imaginary part of the complex permittivity is referred to as dielectric loss in general.

This dielectric relaxation occurs at a specific frequency band depending on the size, structure, and the like of the cell, and the number of the dielectric relaxations depends on the number of major interfaces included in the cell. For example, in a cell such as a red blood cell without a cell nucleus, the number of the dielectric relaxations is one, and in a nucleated cell with one or more nuclei, the number of the dielectric relaxations is two or more.

As described above, the real part and the imaginary part of the complex permittivity of the cell depend on the frequency of the electric field. This is referred to as "dielectric dispersion".

2. Consideration of Dielectric Spectrum of Blood Coagulation System

[2-1. Method of Experiment]

The reaction was started by adding thrombin to model blood and the model blood just after the addition of the thrombin thereto was introduced into a sample introduction portion to measure the permittivity (the real part of the complex permittivity) in a blood coagulation system.

The used model blood was prepared by mixing bovine-derived fibrinogen (Sigma Chem) with an erythrocyte suspension, which is prepared by washing preserved rabbit blood (Kohjin Bio Co., Ltd.) with PBS, and adjusting hematocrit to 25[%] and the concentration of fibrinogen to 0.22[%].

Regarding the thrombin, bovine-derived thrombin (Sigma Chem) was adjusted to 0.01[%] (10 [units/ml]) thrombin, and 10 [μl] (that is, 100 ml [units/ml]) or 5 [μl] (that is, 50 ml [units/ml]) was added per 1 [ml] of model blood.

The permittivity was measured by using an impedance analyzer (4294A) (manufactured by Agilent Technologies Inc.). In addition, the frequency range to be measured (hereinafter, also referred to as a measurement frequency range) was set in the range of 40 [Hz] to 110 [Hz], the time interval to be measured (hereinafter, also referred to as a measurement interval) was set to 1 [minute], and the temperature of a target to be measured was set to 37 [° C.].

Figure 3:
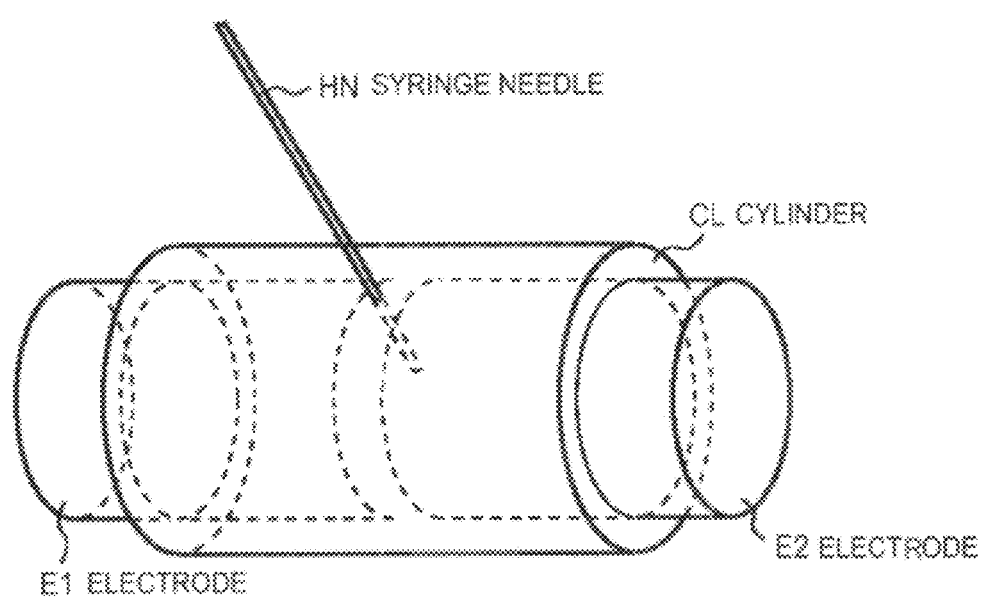
FIG. 3 is a diagram schematically showing the configuration of a sample introduction portion.

The sample introduction portion had a structure shown in FIG. 3. That is, a cylinder CL made of polypropylene was sealed by inserting a pair of gold-plated cylindrical electrodes E1 and E2 into both ends thereof, and a syringe needle HN for applying blood between the electrodes E1 and E2 penetrated the outer wall of the cylinder CL. The portion through which the syringe needle HN passes is blocked by grease, so that the sealed state of the space surrounded by the electrodes E1 and E2 and the cylinder CL is maintained.

[2-2. Experimental Results]

Figure 4:
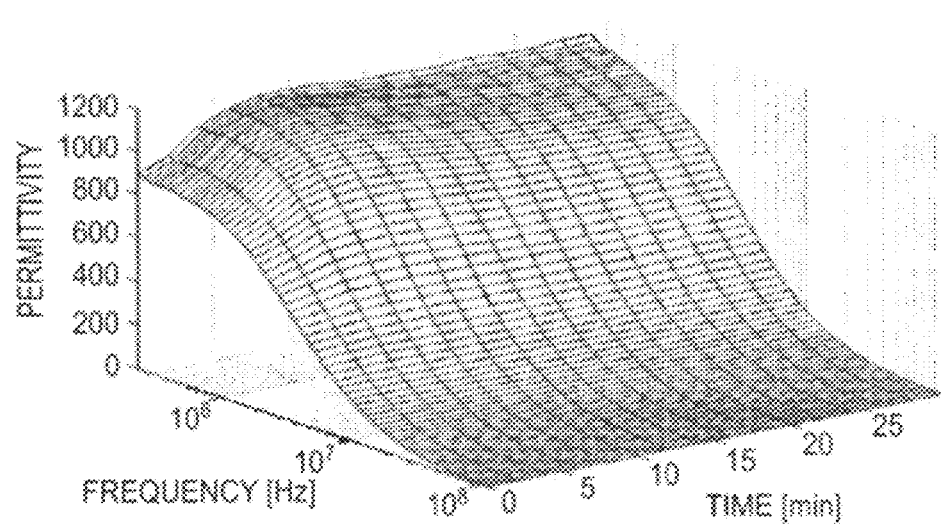
FIG. 4 is a graph showing a dielectric spectrum (when thrombin is applied) of a blood coagulation system which is obtained by an experiment.
Figure 5:
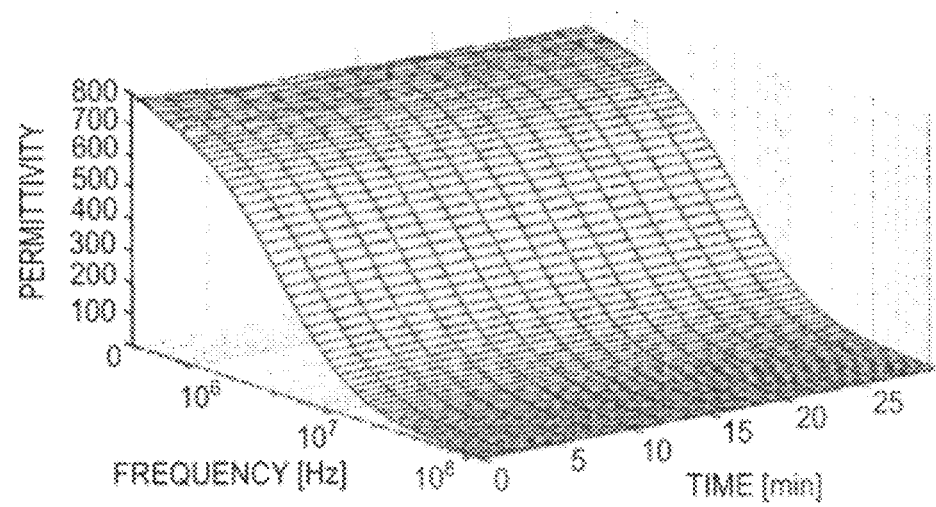
FIG. 5 is a graph showing a dielectric spectrum (when thrombin is applied) of a blood coagulation system which is obtained by an experiment.

FIG. 4 shows the dielectric spectrum which was obtained on the basis of the above-described method of the experiment, and FIG. 5 shows the dielectric spectrum which was observed under the same conditions as in the above-described method of the experiment under the state in which thrombin was not added to model blood. FIG. 4 shows the dielectric spectrum when 10 [μl] of thrombin was added per 1 [ml] of model blood.

When comparing FIG. 4 with FIG. 5, it was possible to observe the dielectric relaxation in the coagulation system of the model blood as in a case of normal cell suspension, and an increase in the dielectric response thereof with the advance of coagulation (with the lapse of time) was observed.

Figure 6:
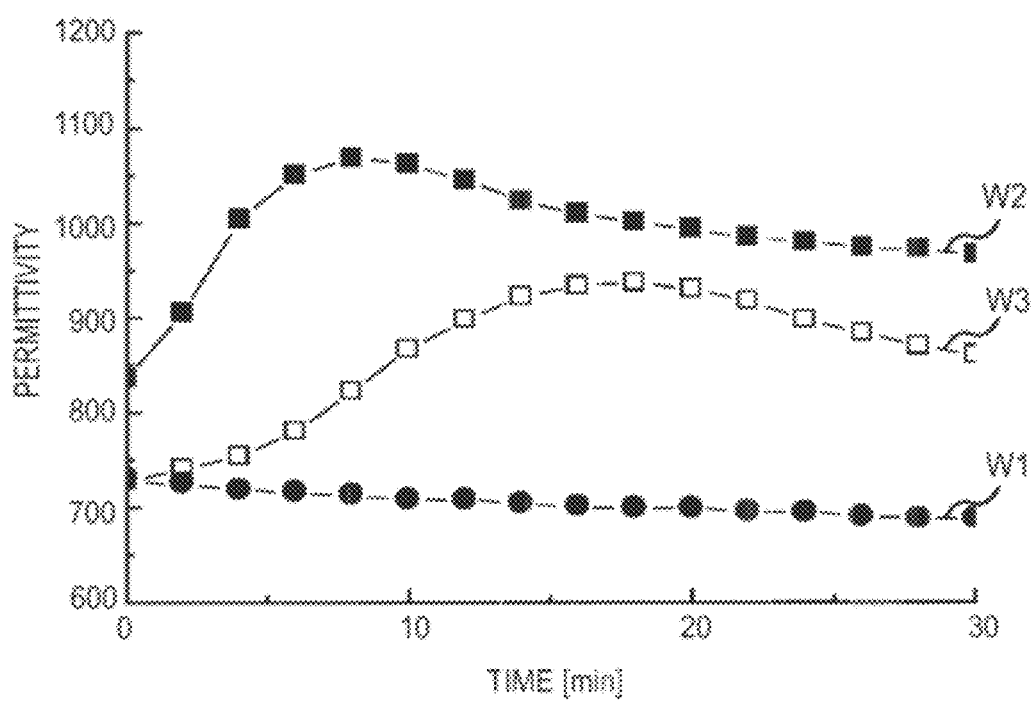
FIG. 6 is a graph showing a temporal change in permittivity (case of model blood) at a specific frequency.

Here, a temporal change in permittivity corresponding to a specific frequency (here, 758 [kHz]) is shown in FIG. 6. The curve W1 in FIG. 6 represents a case in which thrombin was not added to model blood (two-dimensional graph made by cutting out the portion of 758 [kHz] in FIG. 5).

The curve W2 represents a case in which 10 [μl] of thrombin was added per 1 [ml] of model blood (two-dimensional graph made by cutting out the portion of 758 [kHz] in FIG. 4). The curve W3 represents a case in which 5 [μl] of thrombin was added per 1 [ml] of model blood (two-dimensional graph made by cutting out the portion of 758 [kHz] (not shown) as in FIG. 4).

As is clear from the curve W2, the peak of the permittivity was observed after about 8 [minutes] from the point of time at which thrombin was added. In addition, as is clear from the curve W3, when the amount of thrombin was reduced by half, the time at which the peak of the permittivity was shown shifted, and the peak was observed after about 18 [minutes] from the point of time at which thrombin was added.

When 10 [μl] of thrombin was added per 1 [ml] of model blood and when 5 [μl] of thrombin was added per 1 [ml] of the model blood, dynamic viscoelasticity was also measured (rheological measurement) by using a free damped oscillation-type rheometer. The results of this measurement are shown in FIG. 7.

Figure 7A:
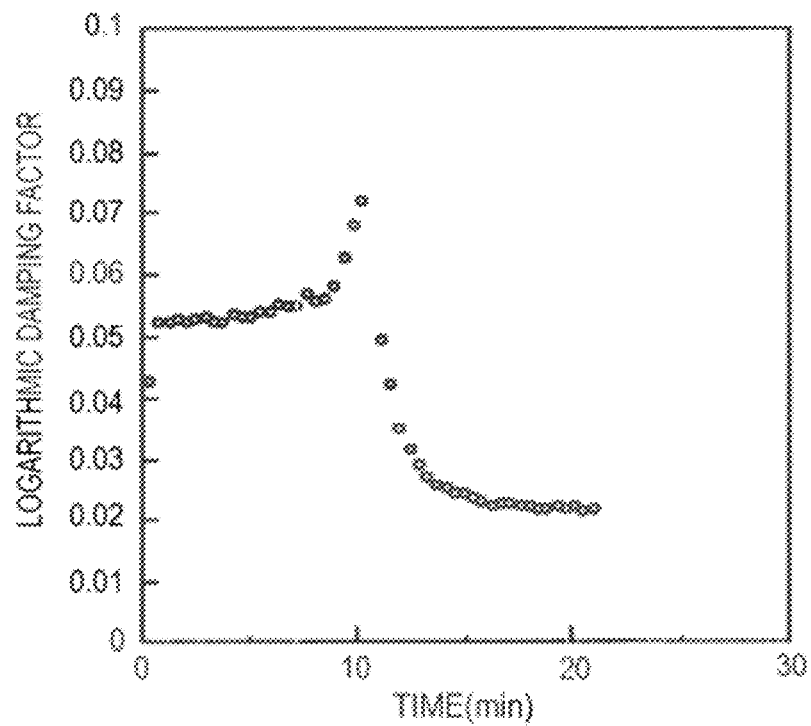
FIG. 7 shows graphs showing the results of a measurement of dynamic viscoelasticity using a damped oscillation-type rheometer.
Figure 7B:
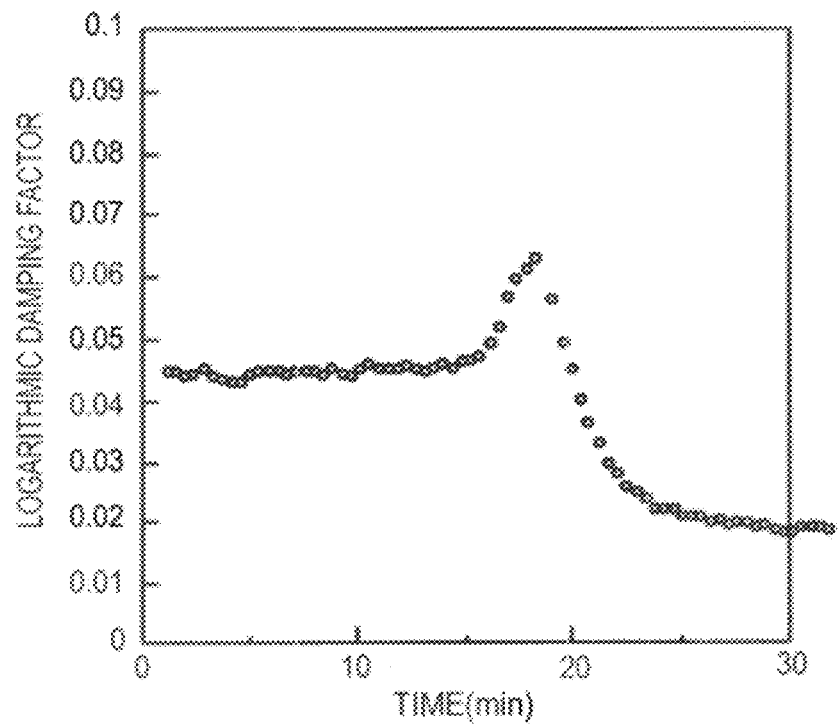

In FIG. 7, the graph (A) shows a case in which 10 [μl] of thrombin was added per 1 [ml] of model blood and the graph (B) shows a case in which 5 [μl] of thrombin was added per 1 [ml] of model blood. The peaks in FIGS. 7(A) and 7(B) show the timing at which certain viscoelastic characteristics are exhibited. That is, the peaks represent the timing (hereinafter, also referred to as a viscoelasticity manifestation timing) at which blood starts to clot from the viewpoint of (dynamic) viscoelasticity.

The actual blood coagulation system is subjected to complicated biological reactions in which a number of coagulation factors relate to each other, but eventually, fibrinogen in blood is converted into fibrin due to the involvement of thrombin. A portion in which fibrinogen is changed into fibrin can be determined as a process taking a substantial role of blood clotting.

In greater detail, in this process, fibrinogen is changed into fibrin monomers due to the involvement of thrombin and they are polymerized with each other to be changed into fibrin polymers. The fibrin polymers are cross-linked to each other due to the involvement of a XIII-th factor to be changed into stabilized fibrin, so that substantial blood coagulation occurs.

Accordingly, the viscoelasticity manifestation timing which is obtained as a peak by a measurement of a free damped oscillation-type rheometer (the peak may not be obtained, but in that case, the point of time at which the logarithmic decrement starts to be reduced is employed) is thought to correspond to the process in which fibrin monomers are polymerized with each other to be changed into fibrin polymers or the process in which these fibrin polymers are cross-linked to each other to be changed into stabilized fibrin. At least, the timing is later than a point of time at which the thrombin starts to be involved with respect to fibrinogen.

As is clear from FIG. 7, as in the case of the dielectric spectrum shown in FIG. 6, after about 8 [minutes] from the point of time at which thrombin was added (FIG. 7 (A)), and after about [minutes] from the point of time at which a half of the thrombin was added (FIG. 7B)), a rapid increase in the viscoelastic modulus (viscoelasticity manifestation timing) was observed.

Figure 8:
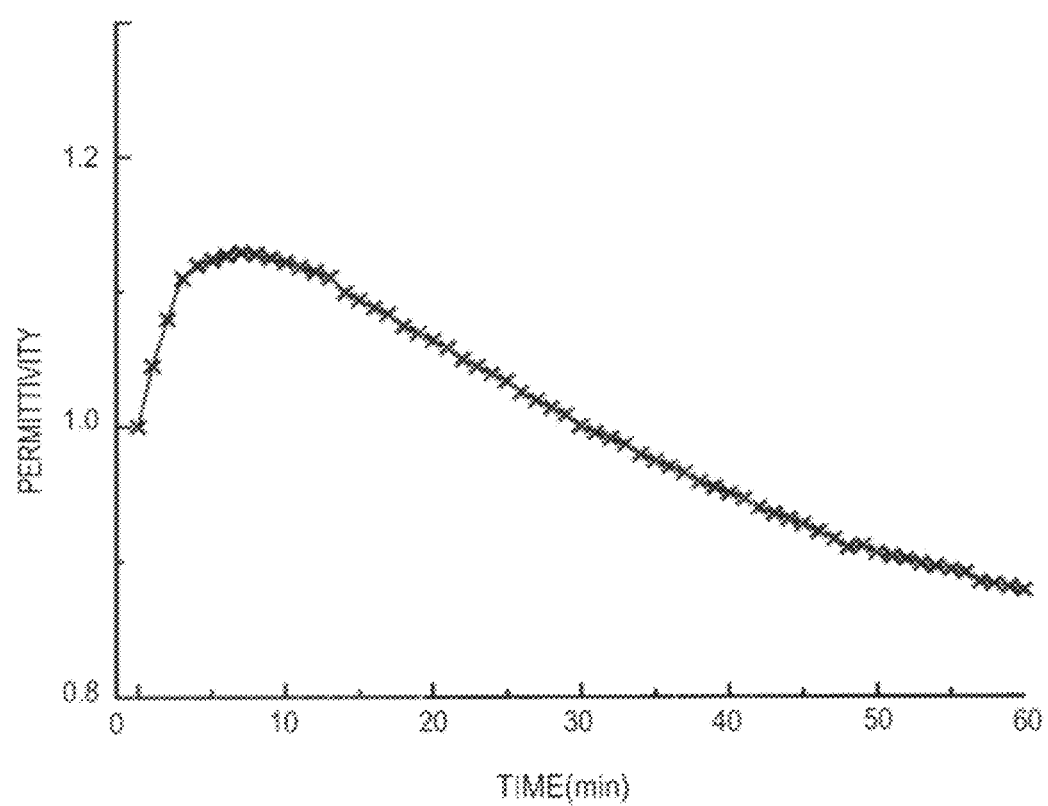
FIG. 8 is a graph showing a temporal change in permittivity (case of human blood) at a specific frequency.

Accordingly, it was discovered that a temporal change in permittivity reflects the blood coagulation system. Particularly, a noteworthy point is that when the permittivity is measured, as is clear from the comparison of FIG. 6 with FIG. 7, the process before the viscoelasticity manifestation timing, which cannot be observed by a free damped oscillation-type rheometer, can be clearly observed. As shown in FIG. 8, this process could be observed also in the case of blood collected from a human.

FIG. 8 shows a temporal change in permittivity corresponding to a specific frequency (here, 758 [kHz]) from just after addition of a coagulation initiator (calcium chloride) to blood which is collected from a terminal of a human in a test tube containing an anticoagulant (citric acid).

As is clear from these experiments, to reflect the process before the viscoelasticity manifestation timing as an increased change in permittivity is to say that the increased change is an index quantitatively showing a degree of the action of the coagulation system before the viscoelasticity manifestation timing (in other words, degree of hypercoagulability or coagulability).

In greater detail, the gradient of the permittivity in the initial stage from just after the start of the measurement up to the peak is large when the viscoelasticity manifestation timing is early (FIG. 6: curve W2), and the gradient is small when the viscoelasticity manifestation timing is late (FIG. 6: curve W3). Accordingly, from the transition of the permittivity in the initial stage up to the peak, the degree of the action of the blood coagulation system (degree of hypercoagulability or degree of coagulability) can be analyzed in detail in a short time.

3. Embodiments

Next, a blood coagulation system analysis device will be explained as an embodiment.

[3-1. Configuration of Blood Coagulation System Analysis Device]

Figure 9:
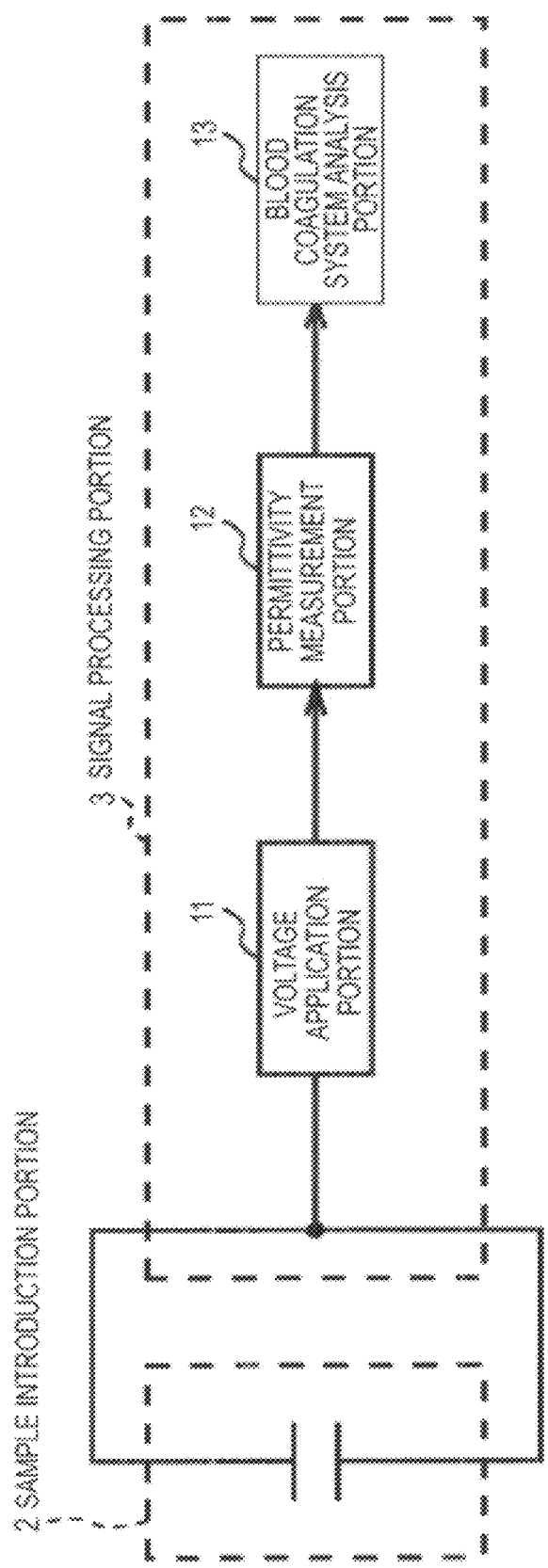
FIG. 9 is a diagram schematically showing the configuration of a blood coagulation system analysis device.

In FIG. 9, the schematic configuration of a blood coagulation system analysis device 1 is shown. This blood coagulation system analysis device 1 has a sample introduction portion 2 and a signal processing portion 3. In this blood coagulation system analysis device 1, a temperature sensor (not shown) and a thermoelectric element (not shown) are provided in the sample introduction portion 2 or the signal processing portion 3. The blood coagulation system analysis device 1 measures the temperature of blood to be measured by using the temperature sensor and gives a signal amount according to this measurement result to the thermoelectric element in order to be able to adjust the temperature of the blood.

The sample introduction portion 2 has a pair of electrodes and human blood is introduced between the electrodes. An anticoagulation effect acts on this human blood, and the anticoagulation effect is ended just before or after introduction of the human blood between the electrodes.

This sample introduction portion 2 can employ, for example, the structure shown in FIG. 3. However, the structure of the sample introduction portion 2, or the shape or material of each portion is not limited to that shown in FIG. 3. For example, a sample introduction portion can be employed which has a structure in which both ends of a tube which has a sectional surface having a polygonal shape (triangular, square or polygonal) are sealed and a pair of electrodes and wirings connected thereto are printed on one inner surface of the cylinder. The main point is that the anticoagulation effect acting on the blood can be ended just before or after introduction of the blood between the electrodes and the blood can be allowed to stay between the electrodes for a predetermined time period.

The signal processing portion 3 is configured to include a voltage application portion 11, a permittivity measurement portion 12, and a blood coagulation system analysis portion 13.

The voltage application portion 11 applies an alternating voltage while judging a point of time at which a command to start a measurement is received or a point of time at which power is applied as a start point.

In greater detail, the voltage application portion 11 applies, at set measurement intervals, an alternating voltage of a frequency (hereinafter, also referred to as a frequency to be considered) which is set to be considered to the pair of electrodes disposed in the sample introduction portion 2.

Regarding the measurement interval and the frequency to be considered, specifically, 1 [minute] and 758 [kHz] used in the above-described experiments can be employed. However, these numerical values are examples, and the measurement interval and the frequency to be considered are not limited to the numerical values. In addition, the measurement interval and the frequency to be considered can be set to various values via input means such as a mouse or a keyboard.

The dielectric measurement portion 12 measures permittivity while judging a point of time at which a command to start a measurement is received or a point of time at which power is applied as a start point.

In greater detail, the dielectric measurement portion measures a current or impedance between the pair of electrodes disposed in the sample introduction portion 2 at predetermined intervals and calculates the permittivity from the measured value. In the calculation of the permittivity, a known function or relational expression showing the relationship between the current or impedance and the permittivity is used.

Data (hereinafter, also referred to as permittivity data) showing the permittivity corresponding to the frequency to be considered is given to the blood coagulation system analysis portion 13 from the permittivity measurement portion 12 at measurement intervals.

The blood coagulation system analysis portion 13 starts a blood coagulation system analysis process when receiving the permittivity data after the point of time at which the anticoagulation effect of human blood is ended among the permittivity data given from the permittivity measurement portion 12.

In order to determine a point of time at which the anticoagulation effect of human blood is ended, a method of setting a value, which is greater than the permittivity which is shown before the anticoagulation effect is ended by a predetermined amount, as a threshold and judging a point of time, at which permittivity data showing the permittivity equal to or greater than the threshold is received, as a point of time at which the anticoagulation effect of human blood is ended is employed.

When this method is employed, schematically, in a case in which the anticoagulation effect of the human blood is ended after introduction between the electrodes of the sample introduction portion 2, a point of time at which first permittivity data is received from the point of time at which the effect is ended is judged as a start point of the analysis process. On the other hand, in a case in which the anticoagulation effect of the human blood is ended just before introduction between the electrodes of the sample introduction portion 2, a point of time at which permittivity data which is given first from the permittivity measurement portion 12 is received is judged as a start point of the analysis process.

In the blood coagulation system analysis portion 13, a period until a set period elapses from the point of time at which the blood coagulation system analysis process is started is set as an analysis period. The blood coagulation system analysis portion 13 detects a straight line most approximate to permittivities which are shown by a plurality of pieces of permittivity data received (measured) within this analysis period. In addition, the blood coagulation system analysis portion 13 obtains the gradient of the detected straight line as a parameter showing an amount of increase in permittivity before the viscoelasticity manifestation timing, and predicts the viscoelasticity manifestation timing from the gradient.

Regarding this prediction, the greater the gradient of the straight line, the earlier the viscoelasticity manifestation timing, and for example, the prediction is performed on the basis of a database in which the gradient of the straight line and the viscoelasticity manifestation timing are associated with each other or a function showing the relationship (regularity) between the gradient of the straight line and the viscoelasticity manifestation timing.

When predicting the viscoelasticity manifestation timing, the blood coagulation system analysis portion 13 notifies of one or both of the prediction results and the permittivity used in the prediction.

This notification is performed by, for example, performing plotting and displaying on a monitor or printing on a predetermined medium.

[3-2. Order of Blood Coagulation System Analysis Process]

Figure 10:
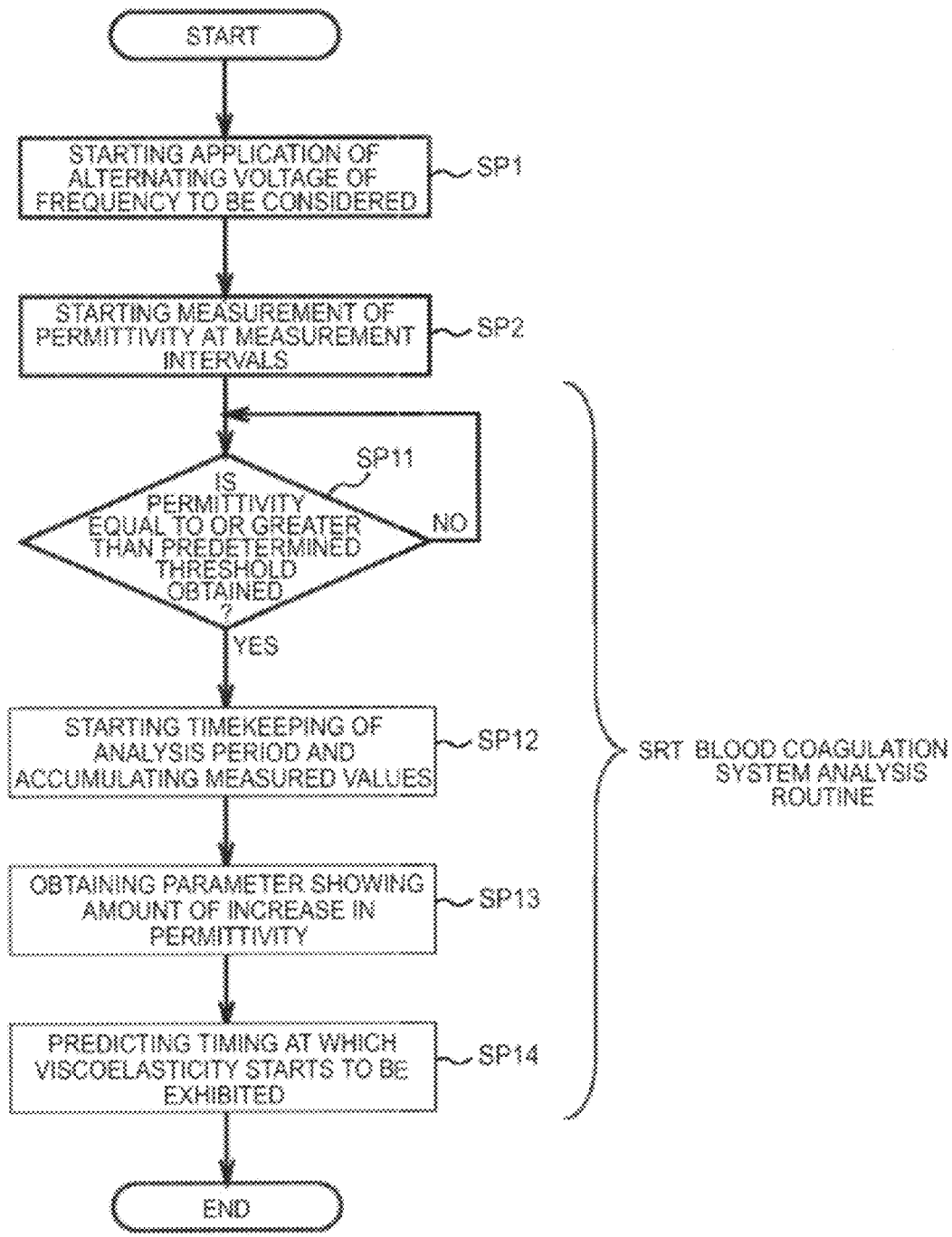
FIG. 10 is a flowchart showing the order of a blood coagulation system analysis process.

Next, the procedure of the blood coagulation system analysis process will be described using the flowchart shown in FIG. 10.

That is, the blood coagulation system analysis device 1 sets, for example, the time when a command to start a measurement is received or the time when power is applied as a trigger to deploy a program stored in a ROM in a RAM, and advances the process to Step SP1 to start the blood coagulation system analysis process.

In Step SP1, the blood coagulation system analysis device 1 prompts the voltage application portion 11 to start the application of an alternating voltage of a frequency to be considered to the pair of electrodes disposed in the sample introduction portion 2 at set measurement intervals, and advances the process to the next Step SP2.

In Step SP2, the blood coagulation system analysis device 1 prompts the permittivity measurement portion 12 to measure the permittivity, and advances the process to the following sub-routine (hereinafter, also referred to as a blood coagulation system analysis routine) SRT. The blood coagulation system analysis device prompts the blood coagulation system analysis portion 13 to start the analysis of the blood coagulation system.

That is, in Step SP 11 of the blood coagulation system analysis routine, the blood coagulation system analysis portion 13 awaits permittivity data showing the permittivity equal to or greater than a predetermined threshold. In this Step SP11, when receiving permittivity data equal to or greater than the predetermined threshold, the blood coagulation system analysis portion 13 judges this moment as the point of time at which the anticoagulation effect of human blood is ended, and advances the process to the next Step SP12.

In Step SP12, the blood coagulation system analysis portion 13 starts timekeeping of the set analysis period, and accumulates permittivity data which is given from the permittivity measurement portion 12 until the set analysis period elapses.

Next, the blood coagulation system analysis portion 13 detects a straight line most approximate to permittivities which are shown by the permittivity data accumulated within the analysis period, and obtains a gradient of the straight line as a parameter showing an amount of increase in permittivity before the viscoelasticity manifestation timing.

In addition, in Step SP14, the blood coagulation system analysis portion 13 predicts the viscoelasticity manifestation timing from the parameter (gradient of the initial waveform of the dielectric spectrum) obtained in Step SP13, and then ends the blood coagulation system analysis process.

In this manner, the blood coagulation system analysis device 1 executes the blood coagulation system analysis process in accordance with the program deployed in the RAM.

[3-3. Effects and the like]

In the above-described configuration, this blood coagulation system analysis device 1 applies an alternating voltage of a frequency to be considered at predetermined time intervals to the pair of electrodes which is opposed to each other with the position, at which blood is to be positioned, interposed therebetween (see FIG. 9).

In addition, the blood coagulation system analysis device 1 measures a permittivity of the blood which is positioned between the pair of electrodes at predetermined time intervals after the anticoagulant effect acting on the blood is ended, and analyzes the degree of the action of the blood coagulation system from the measurement result.

The blood coagulation system is observed as a temporal change in permittivity before the viscoelasticity manifestation timing (timing at which blood starts to clot from the viewpoint of viscoelasticity (in greater detail, at least timing at which active polymerization of fibrin monomers starts)) (see FIGS. 6 and 7).

Regarding this point, since the blood coagulation system analysis device 1 uses the permittivity which is measured after the anticoagulant effect acting on the blood is ended, the process before the viscoelasticity manifestation timing which cannot be observed by a free damped oscillation-type rheometer can be clearly observed.

That is, this blood coagulation system analysis device 1 can quantitatively determine the blood coagulation factor acting at an early stage before the viscoelasticity manifestation timing by a temporal change in permittivity before the viscoelasticity manifestation timing.

It is known that a series of coagulation reactions causing venous thrombus may be started due to a gradual activation of a IX-th blood coagulation factor on a red blood cell membrane (Makoto KAIBARA, Experimental Medicine Vol. 22, No. 13, 2004, pp. 1869-1874).

In addition, as a conventional measurement method relating to the blood coagulation system, activated partial thromboplastin time (APTT) has been widely known as described above.

However, this APTT is not for observing a degree of ease of clotting of blood, but for observing in a fragmentary manner (qualitatively) whether or not coagulation is completed within a time considered as normal under the conditions where the coagulation reaction is accelerated by adding an excessive amount of a coagulation initiator to evaluate the difficulty of clotting of blood (bleeding tendency). Accordingly, the APTT is useless when the ease of clotting of blood (thrombotic tendency) such as venous thrombosis relatively gradually progressing due to bloodstream stagnation in the vein becomes a problem, and a risk of the disease cannot be evaluated.

This blood coagulation system analysis device 1 can quantitatively determine the blood coagulation factor acting at an early stage by a temporal change in permittivity before the viscoelasticity manifestation timing. Accordingly, this blood coagulation system analysis device 1 can evaluate a risk or perform monitoring of diseases relating to the blood coagulation with higher accuracy than in a conventional method of determining in a fragmentary manner (qualitatively) whether or not coagulation is completed within a time considered as normal. Evaluating the risk of diseases is very useful also from the viewpoint of preventive medicine.

For example, since the operation is a risk factor of onset of venous thromboembolism, risk determination after the operation and judgment for medication based on the determination can be easily performed. Since advancing age, obesity, smoking, pregnancy, and the like are also risk factors for onset of venous thromboembolism, risk determination of these and judgment for medication based on the determination can be easily performed. In addition, in the case of diabetic patients, hypercoagulability is often seen and thus judgment for medication can be easily performed by determining the degree thereof.

In the analysis of the blood coagulation system analysis device 1 of this embodiment, the viscoelasticity manifestation timing is predicted from the parameter showing the amount of increase in permittivity before the viscoelasticity manifestation timing. Accordingly, this blood coagulation system analysis device 1 can not only show a trend of the blood coagulation system before the viscoelasticity manifestation timing as a change in permittivity on the display portion, but also rapidly show the viscoelasticity manifestation timing which is predicted from the change in permittivity.

Generally, the viscoelasticity manifestation timing requires several tens [minutes] from the start of the coagulation system, but showing the viscoelasticity manifestation timing in several [minutes] is particularly useful from the viewpoint of monitoring of diseases or evaluation of a risk.

According to the above-described configuration, the blood coagulation system analysis device 1 was used to analyze the action of the blood coagulation system at an early stage by a temporal change in permittivity after the anticoagulant effect acting on blood is ended. Accordingly, it is possible to not only perform monitoring of diseases which could not be performed by a conventional measurement method relating to the blood coagulation system, but also evaluate a risk of the diseases. As a result, it is possible to realize the blood coagulation system analysis device 1 capable of increasing the degree of accuracy of the analysis in comparison to the conventional case.

4. Other Embodiments

In the above-described embodiment, human peripheral blood (venous blood) was used as a sample to be measured. However, the sample is not limited to human blood and may be blood of an animal other than a human. The sample may be arterial blood.

In the above-described embodiment, an alternating voltage of a frequency to be considered was applied to the pair of electrodes disposed in the sample introduction portion 2. However, the frequency of the alternating voltage to be applied may be a frequency for each predetermined or whole width in a certain band including the frequency to be considered.

In this case, data showing the permittivity corresponding to a plurality of frequencies is given to the blood coagulation system analysis portion 13 at measurement intervals from the permittivity measurement portion 12. Accordingly, the blood coagulation system analysis portion 13 can correct the above permittivity by using the permittivity corresponding to a plurality of frequencies.

Figure 11:
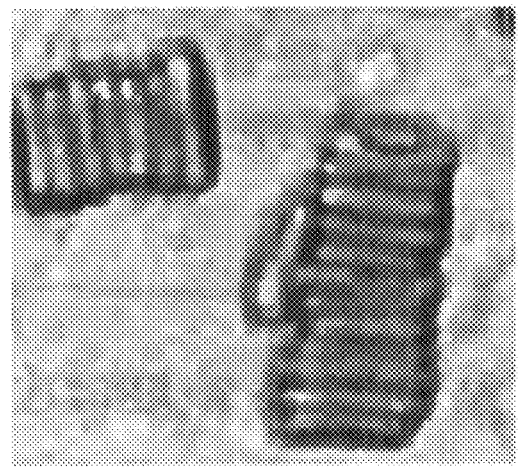
FIG. 11 is a photograph showing red blood cells forming rouleau.

However, as shown in FIG. 11, red blood cells are often linked together irregularly or in the form of rouleau and agglutinate (form a lump). When red blood cells agglutinate, the permittivities of the red blood cells are known to increase as shown in FIG. 12.

Figure 12:
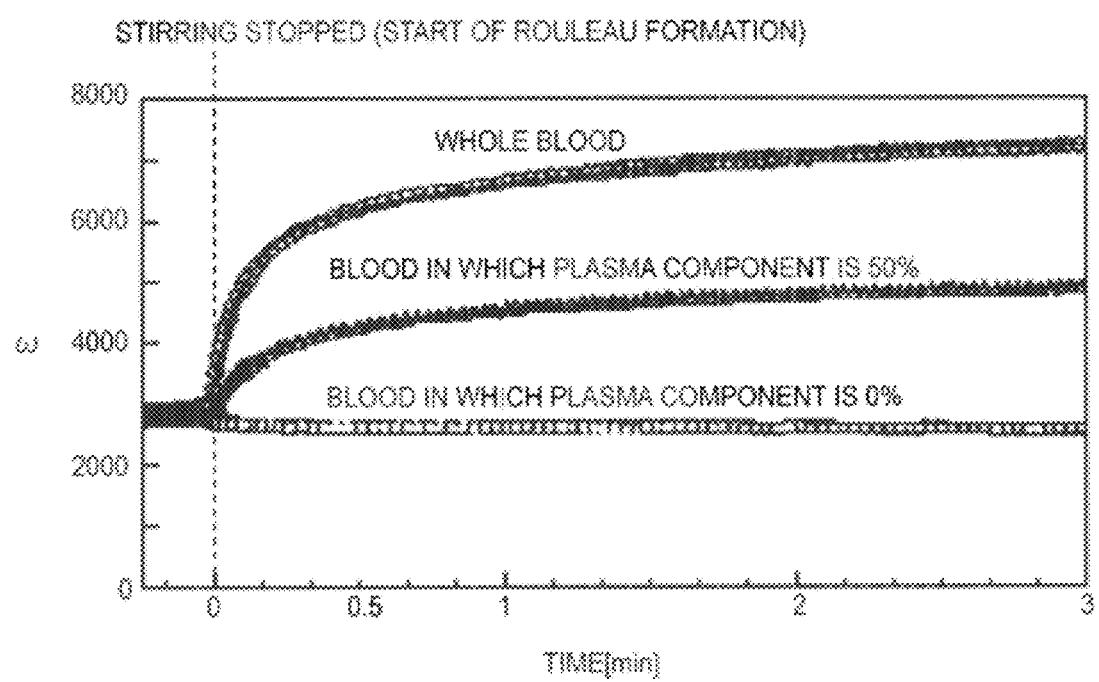
FIG. 12 is a graph showing a temporal change in permittivity after stirring is stopped.

FIG. 12 quotes the measurement result of a change in permittivity after stopping stirring of whole blood, blood in which a plasma component is 50%, and blood in which a plasma component is 0% from A. Irimajiri et al, elsevier science, Biochim. Biophys, vol. 1290, p. 207-209.

When a change ratio of permittivity is viewed as a ratio between the permittivity and permittivity at a reference time, it is found that a temporal change in permittivity resulting from the agglutination of red blood cells exhibits a frequency dependency (a difference in a temporal change in permittivity due to a difference in a frequency) that is smaller than that of a temporal change in permittivity resulting from blood coagulation.

Accordingly, by taking a difference between the change ratio of the permittivity corresponding to a specific frequency and the change ratio of the permittivity corresponding to a frequency different from the above frequency, it is possible to reduce a degree of influence of the permittivity resulting from the agglutination of red blood cells while leaving a change in permittivity resulting from blood coagulation.

Figure 13:
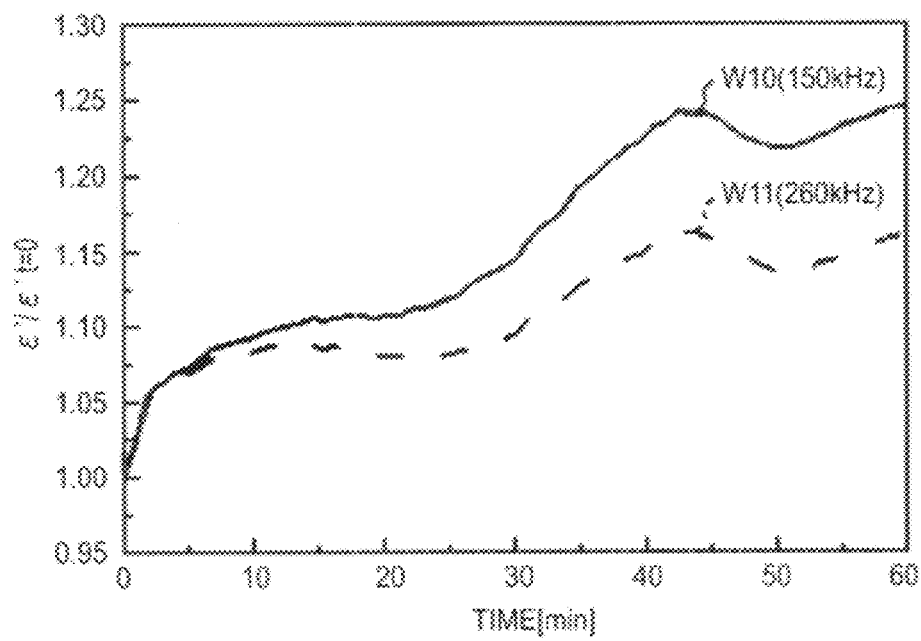
FIG. 13 is a graph showing temporal changes when permittivities corresponding to two specific frequencies are each expressed as a ratio between the permittivity and permittivity at a reference time.
Figure 14:
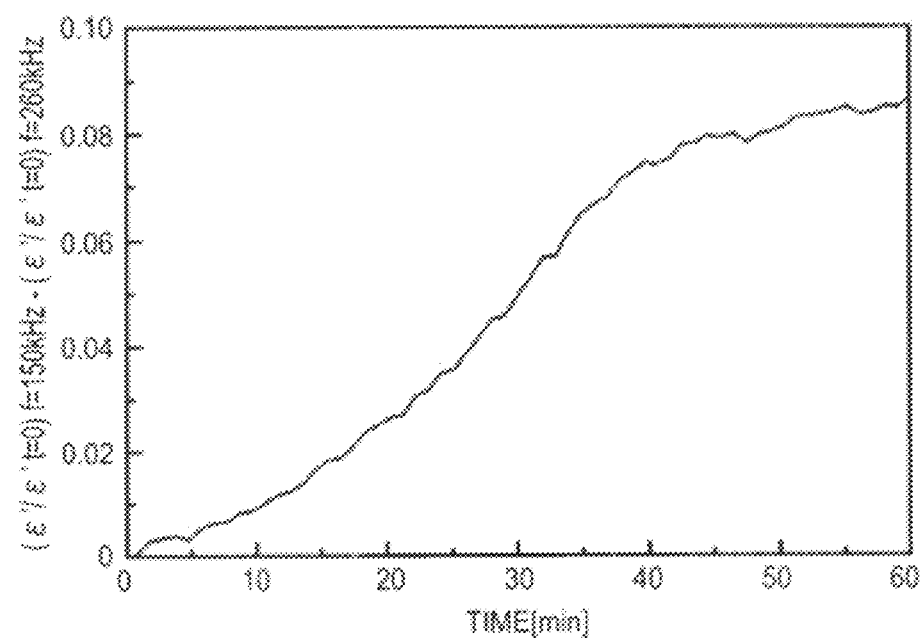
FIG. 14 is a graph showing a temporal change when a difference between change ratios of the permittivities each corresponding to each frequency is taken.

Here, FIGS. 13 and 14 show the experimental results. FIG. 13 shows temporal changes when permittivities corresponding to two specific frequencies are each expressed as a ratio between the permittivity and permittivity at a reference time just after human venous blood is collected in a test tube containing an anticoagulant (citric acid) and a coagulation initiator (calcium chloride) is added to the blood.

The specific frequencies are 150 [kHz] (the waveform W10 shown by the solid line in FIGS. 13) and 260 [kHz] (the waveform W11 shown by the broken line in FIG. 13), and the permittivity at a reference time is a permittivity ($\epsilon'_{t=0}$) which is initially measured.

FIG. 14 shows a temporal change when a difference between change ratios of the permittivities each corresponding to each frequency is taken (that is, a difference between the waveform W10 and the waveform W11 shown in FIG. 13).

This experiment was performed under the same conditions as those in the experiments relating to the above-described experimental results (FIG. 4, FIG. 5, FIG. 8). That is, the measurement frequency range was set in the range of 40 [Hz] to 110 [Hz], the measurement interval was set to 1 [minute], the temperature of a target to be measured was set to 37[° C.], and the permittivity was measured by using an impedance analyzer (4294A) (manufactured by Agilent Technologies Inc.).

As can be seen from this FIG. 13, when the permittivity corresponding to a specific frequency and the permittivity corresponding to a frequency different from the above frequency are each viewed as a ratio between the permittivity and permittivity at a reference time, the shorter the measurement time, the more the permittivities overlap. This is because with a short time period, the influence of a change in permittivity resulting from the agglutination of red blood cells is relatively large and this influence exhibits a relatively small frequency dependency. On the other hand, with a long time period, the influence of a change in permittivity resulting from blood coagulation is relatively large and also exhibits a relatively large frequency dependency.

As can be seen from this FIG. 14, the difference between change ratios corresponding to the respective frequencies has a tendency to linearly increase since the degree of influence of the permittivity resulting from the agglutination of red blood cells is reduced while leaving the degree of influence of a change in permittivity resulting from blood coagulation.

Figure 15:
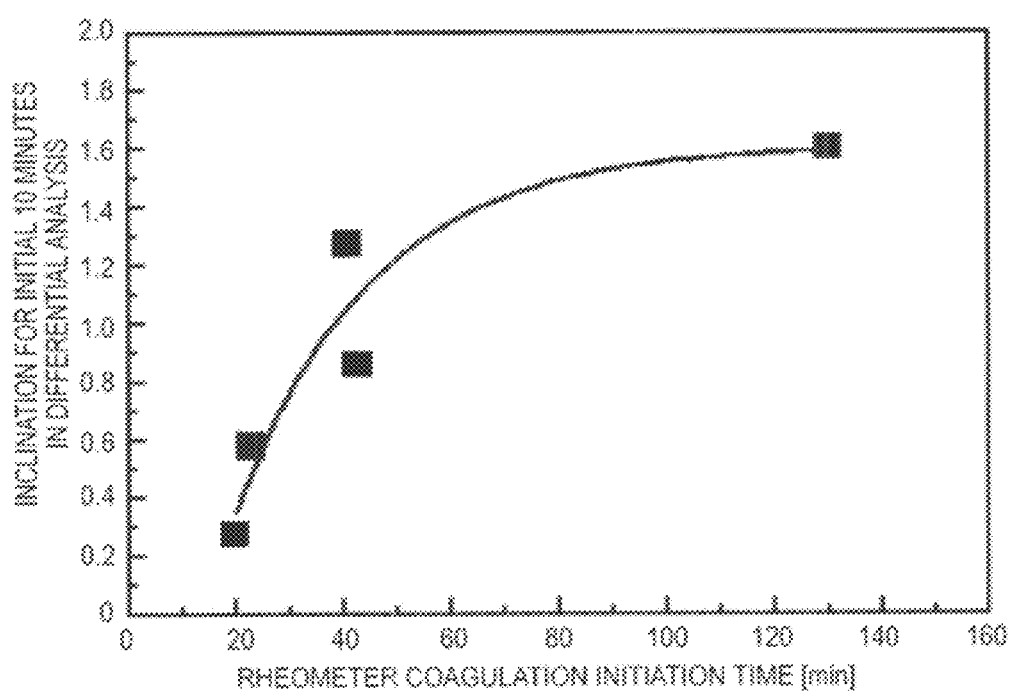
FIG. 15 is a graph showing an inclination of a temporal change in the difference between change ratios of the permittivities corresponding to two frequencies and the coagulation initiation timings obtained by a rheological measurement.

FIG. 15 shows another experimental result. This FIG. 15 shows the relationship between analysis using the difference between change ratios of permittivities corresponding to two frequencies and the coagulation initiation timing obtained by a rheological measurement.

The plots of FIG. 15 show, regarding five healthy people, a difference between change ratios of permittivities corresponding to two frequencies (150 [kHz] and 260 [kHz]) after 10 minutes from the start of the measurement. The waveform of FIG. 15 is an optimum approximate curve based on these plots.

As can be seen from FIG. 15, there is obtained a tendency that the shorter the coagulation initiation timing obtained by a rheological measurement, the smaller the inclination of the difference between change ratios of the permittivities corresponding to the two frequencies. However, this tendency depends on the frequency to be a measurement target or a difference in the structure or material of the electrodes which are employed in the sample introduction portion 2.

In this manner, the blood coagulation system analysis portion 13 divides measured values (permittivities corresponding to the two specific frequencies), which are given from the permittivity measurement portion 12 at predetermined intervals, by expressing them as a ratio between the permittivity and permittivity at a reference time, thereby being capable of focusing precisely on the temporal change in permittivity reflecting the initial process of the blood coagulation reaction. As a result, it is possible to further improve the degree of accuracy of the analysis of the permittivity resulting from blood coagulation.

As another example, by using a permittivity other than the permittivity corresponding to a frequency to be considered, the permittivity corresponding to the frequency to be considered may be corrected. For example, a correction method of correcting the gradient of permittivity corresponding to the frequency to be considered can be employed so that the larger the degree of bias in the gradient of permittivity corresponding to a frequency approximate to the frequency to be considered, the side where the bias of the gradient is large is weighted. The above-described correction method is an example, and other types of correction methods can be employed.

As a method of applying alternating voltages of a plurality of frequencies, any one of a so-called frequency range method, a frequency superposition method, and a time range method can be employed and a method in which these methods are combined can also be employed.

The frequency range method is a method of applying an alternating voltage while rapidly switching a frequency for each predetermined or the whole width in a frequency band to be measured. The frequency superposition method is a method of applying an alternating voltage in which all or some frequency components in a frequency band to be measured are mixed. The time range method is a method of applying a step voltage. In this time range method, a process is needed for Fourier-transforming the current responding to an alternating voltage in which a plurality of frequency components is mixed as a function of time and detecting the frequency dependency.

As a wave in which a plurality of frequency components is mixed, for example, a derivative Gaussian wave, a surface transverse wave (STW), a Rayleigh wave (Surface Acoustic Wave), a Bleustein-Gulyaev-Shimizu (BGS) wave, a Lamb wave, a surface skimming bulk wave, a shear horizontal (SH) wave, or the like can be applied.

In addition, in the above-described embodiments, as a parameter showing an amount of increase in permittivity before the viscoelasticity manifestation timing, the gradient of a straight line most approximate to the permittivities which are measured within the analysis period was applied. However, this parameter is not limited to the gradient of the straight line. For example, an average of change ratios of the permittivities which are measured within the analysis period can be used.

In greater detail, the blood coagulation system analysis portion 13 takes, for each reception of permittivity data from the permittivity measurement portion 12 within the analysis period, a difference between permittivities which are shown by the above permittivity data and permittivity data received just before the above point of time of reception. This difference becomes an amount of increase in permittivity per observation interval.

The blood coagulation system analysis portion 13 obtains the amount of increase in permittivity per observation interval until the analysis period elapses, and when the analysis period elapses, the blood coagulation system analysis portion obtains an average of the obtained amounts of increase in permittivity as a parameter showing an amount of increase in permittivity before the viscoelasticity manifestation timing.

In this manner, as a parameter showing an amount of increase in permittivity before the viscoelasticity manifestation timing, an average of change ratios of the permittivities which are measured within the analysis period can be applied. Another other than the average of change ratios of the permittivities or the gradient of the straight line can be used as a parameter showing an amount of increase in permittivity before the viscoelasticity manifestation timing.

In addition, in the above-described embodiments, from the parameter showing an amount of increase in permittivity before the viscoelasticity manifestation timing, the viscoelasticity manifestation timing was predicted. However, the analysis item is not limited to the prediction of the viscoelasticity manifestation timing. For example, a risk of thrombus can be evaluated.

In this evaluation, the larger the parameter (the inclination of the gradient of the straight line most approximate to the permittivities which are measured within the analysis period or the average of change ratios of permittivities) showing an amount of increase in permittivity before the viscoelasticity manifestation timing, the higher the risk of thrombus. In greater detail, the evaluation is performed on the basis of, for example, a database in which the parameter and the risk of thrombus are associated with each other or a function showing the relationship (regularity) between the parameter and the risk of thrombus. The risk of thrombus can also be evaluated in a step-by-step manner.

INDUSTRIAL APPLICABILITY

The invention can be used in biological experiments, monitoring, or bioindustries such as diagnosis or preparation of medicine.

REFERENCE SIGNS LIST

1: BLOOD COAGULATION SYSTEM ANALYSIS DEVICE
2: SAMPLE INTRODUCTION PORTION
3: SIGNAL PROCESSING PORTION
11: VOLTAGE APPLICATION PORTION
12: PERMITTIVITY MEASUREMENT PORTION
13: BLOOD COAGULATION SYSTEM ANALYSIS PORTION
CL: CYLINDER
E1, E2: ELECTRODE
HN: SYRINGE NEEDLE

The invention claimed is:
1. A blood coagulation system analysis device comprising:
a cylinder;
a pair of electrodes opposed to each other and inserted into opposite ends of the cylinder with a position at which a sample of whole blood is positioned interposed therebetween; and
circuitry configured to
apply an alternating voltage to the pair of electrodes;
measure a permittivity of the sample of whole blood; and
analyze a degree of action of a blood coagulation system by determining the permittivity of blood measured at predetermined time intervals after an anticoagulant effect acting on the sample of whole blood is ended,
wherein the determination of the anticoagulant effect acting on the sample of whole blood is ended is determined when the permittivity of blood is equal to or greater than the predetermined threshold,
wherein the analyzing includes estimating a viscoelasticity manifestation timing at which viscoelastic characteristics are exhibited and obtain a gradient of a straight line as a parameter showing an amount of increase in permittivity of a frequency to be considered within a predetermined time period after the anticoagulant effect acting on the sample of whole blood is ended,
wherein the analyzing includes dividing permittivity of a first frequency and permittivity of a second frequency, different from the first frequency, within a predetermined time period after the anticoagulant effect acting on the sample of whole blood is ended by expressing them as a ratio between the permittivity and permittivity at a reference time to analyze, using the division result, the degree of the action of the blood coagulation system, and
wherein the estimated viscoelasticity manifestation timing at which viscoelastic characteristics predict that the sample of whole blood starts to clot is displayed to monitor patient disease.

2. The blood coagulation system analysis device according to claim 1,
wherein the analyzing includes evaluating a risk of thrombus from the parameter showing an amount of increase in permittivity of a frequency to be considered within a predetermined time period after the anticoagulant effect acting on the sample of whole blood is ended.

3. A blood coagulation system analysis method comprising:

applying an alternating voltage to a pair of electrodes that are opposed to each other and inserted into opposite ends of a cylinder;

measuring permittivity of a sample of whole blood which is positioned between the pair of electrodes;

analyzing a degree of the action of a blood coagulation system by determining the permittivity of blood measured at predetermined time intervals after an anticoagulant effect acting on the sample of whole blood is ended, wherein the determination of the anticoagulant effect acting on the sample of whole blood is ended is determined when the permittivity of blood is equal to or greater than the predetermined threshold, wherein the analyzing includes estimating a viscoelasticity manifestation timing at which viscoelastic characteristics are exhibited and obtaining a gradient of a straight line as a parameter showing an amount of increase in permittivity of a frequency to be considered within a predetermined time period after the anticoagulant effect acting on the sample of whole blood is ended, and wherein the analyzing includes dividing permittivity of a first frequency and permittivity of a second frequency, different from the first frequency, within a predetermined time period after the anticoagulant effect acting on the sample of whole blood is ended by expressing them as a ratio between the permittivity and permittivity at a reference time to analyze, using the division result, the degree of the action of the blood coagulation system; and displaying the estimated viscoelasticity manifestation timing at which viscoelastic characteristics predict that the sample of whole blood starts to clot to monitor patient disease.

4. A non-transitory computer-readable medium storing computer-readable instructions thereon, the computer-readable instructions when executed by a computer cause the computer to perform a method comprising:

applying an alternating voltage to apply an alternating voltage to a pair of electrodes that are opposed to each other and inserted into opposite ends of a cylinder;

measuring permittivity to measure permittivity of a sample of whole blood which is positioned between the pair of electrodes;

analyzing a blood coagulation system to analyze a degree of the action of a blood coagulation system by determining the permittivity of blood which is measured at predetermined time intervals after an anticoagulant effect acting on the sample of whole blood is ended, wherein the determination of the anticoagulant effect acting on the sample of whole blood is ended is determined when the permittivity of blood is equal to or greater than the predetermined threshold, wherein the analyzing includes estimating a viscoelasticity manifestation timing at which viscoelastic characteristics are exhibited and obtaining a gradient of a straight line as a parameter showing an amount of increase in permittivity of a frequency to be considered within a predetermined time period after the anticoagulant effect acting on the sample of whole blood is ended, and wherein the analyzing includes dividing permittivity of a first frequency and permittivity of a second frequency, different from the first frequency, within a predetermined time period after the anticoagulant effect acting on the sample of whole blood is ended by expressing them as a ratio between the permittivity and permittivity at a reference time to analyze, using the division result, the degree of the action of the blood coagulation system; and displaying the estimated viscoelasticity manifestation timing at which viscoelastic characteristics predict that the sample of whole blood starts to clot to monitor patient disease.

5. The blood coagulation system analysis device according to claim 1, wherein the applying includes applying the alternating voltage to the pair of electrodes at predetermined time intervals.

6. The blood coagulation system analysis method according to claim 3, wherein the applying includes applying the alternating voltage to the pair of electrodes at predetermined time intervals.

7. The non-transitory computer-readable medium according to claim 4, wherein the applying includes applying the alternating voltage to the pair of electrodes at predetermined time intervals.

8. The blood coagulation system analysis device according to claim 1, wherein analyzing the degree of the action of the blood coagulation system includes determining whether the anticoagulant effect acting on the sample of whole blood is ended.

9. The blood coagulation system analysis method according to claim 3, wherein analyzing the degree of the action of the blood coagulation system includes determining whether the anticoagulant effect acting on the sample of whole blood is ended.

10. The non-transitory computer-readable medium according to claim 4, wherein analyzing the degree of the action of the blood coagulation system includes determining whether the anticoagulant effect acting on the sample of whole blood is ended.

* * * * *